United States Patent
Sakuma et al.

(10) Patent No.: US 7,078,422 B2
(45) Date of Patent: Jul. 18, 2006

(54) ACTIVATOR FOR PEROXISOME PROLIFERATOR-ACTIVATED RECEPTOR

(75) Inventors: Shogo Sakuma, Saitama (JP); Tsuyoshi Endo, Tokyo (JP); Takashi Kanda, Saitama (JP); Seiichiro Masui, Saitama (JP)

(73) Assignee: Nippon Chemiphar Co., Ltd., Tokyo (JP)

( * ) Notice: Subject to any disclaimer, the term of this patent is extended or adjusted under 35 U.S.C. 154(b) by 401 days.

(21) Appl. No.: 10/472,699

(22) PCT Filed: Feb. 19, 2002

(86) PCT No.: PCT/JP02/01422

§ 371 (c)(1), (2), (4) Date: Sep. 23, 2003

(87) PCT Pub. No.: WO02/076957

PCT Pub. Date: Oct. 3, 2002

(65) Prior Publication Data

US 2004/0152744 A1    Aug. 5, 2004

(30) Foreign Application Priority Data

Mar. 23, 2001    (JP) ............................. 2001-086145

(51) Int. Cl.
- *A61K 31/421*    (2006.01)
- *A61K 31/426*    (2006.01)
- *C07D 263/30*    (2006.01)
- *C07D 277/20*    (2006.01)

(52) U.S. Cl. .................. 514/374; 548/204; 548/236; 548/233; 514/365

(58) Field of Classification Search ................ 514/374, 514/365; 548/204, 236, 233
See application file for complete search history.

(56) References Cited

FOREIGN PATENT DOCUMENTS

WO    WO 02/60898    *    8/2002

OTHER PUBLICATIONS

CAS Abstract provided.*

* cited by examiner

*Primary Examiner*—Kamal A. Saeed
*Assistant Examiner*—Jason M. Nolan
(74) *Attorney, Agent, or Firm*—Reed Smith LLP

(57) ABSTRACT

A phenylacetic acid derivative represented by the general formula (II) (wherein $R^{11}$ and $R^{12}$ each represents hydrogen, $C_{1-8}$ alkyl, $C_{1-8}$ alkoxy, $C_{1-8}$ alkyl substituted by one to three halogen atoms, an optionally substituted phenyl, naphthyl, pyridyl, thienyl, or furyl group, etc.; $X^1$ and $Z^1$ each represents —C(=O)—, —C(=O)NH, —NHC(=O)—, —CH=CH—, a bond, etc.; and $Y^1$ represents a $C_{1-8}$ alkylene chain) or a salt of the derivative; and a PPARδ activator which contains the derivative or salt as the active ingredient

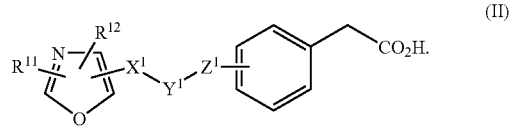

(II)

4 Claims, No Drawings

ACTIVATOR FOR PEROXISOME PROLIFERATOR-ACTIVATED RECEPTOR

CROSS-REFERENCES TO RELATED APPLICATIONS

This application claims priority of Japanese International Application No. PCT/JP02/01422 filed Feb. 19, 2002 which claims the priority of Japanese International Application No. 2001-86145 filed Mar. 23, 2001, the complete disclosures of which are hereby incorporated by reference.

FIELD OF THE INVENTION

The present invention relates to an activator of peroxisome proliferator activated receptor.

BACKGROUND OF THE INVENTION

The peroxisome is a small organ present in the cells of animals and plants, and its matrix contains various enzymes such as catalases. The peroxisome proliferators are a substance inducing proliferation of the peroxisome. Various compounds such as fibrates, herbicides, and phthalic acid plasticizers are known to be able to induce proliferation of peroxisome.

Isseman, et al. have identified a nuclear receptor which is activated by the peroxisome proliferator and given a name of peroxisome proliferator activated receptor (PPAR).—Nature, 347, p 645–650, 1990.

As PPAR, three subtypes such as PPARα, PPARγ and PPARδ have been identified until now.—Proc. Natl. Acad. Sci. USA, 91, p 7335–7359, 1994.

The above-mentioned fibrates have a ligand effect on PPARα and are confirmed to show a strong serum TG (triglyceride) lowering effect in their clinical uses. Further, thiazolidine compounds (Troglitazone, Rosiglitazone, Pioglitazone) useful in the treatment of diabetes are also known as ligands of PPARγ.

As a pharmaceutical having PPARδ activating effect, there are known GW-2433 (Glaxo Wellcome), L-165041 (Merck), and YM-16638 (Yamanouchi Pharmaceutical) each having the following formula:

GW-2433 (Glaxo Wellcome)

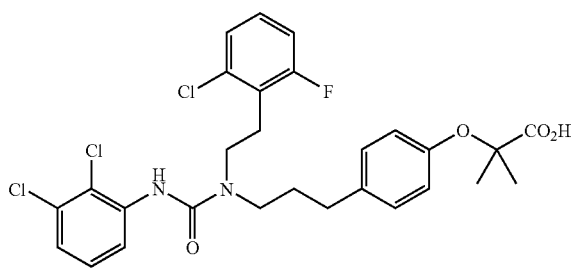

L-165041 (Merck)

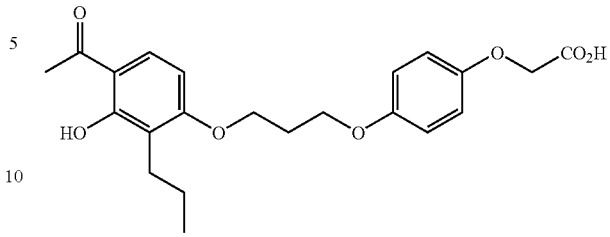

YM-16638 (Yamanouchi Pharmaceutical)

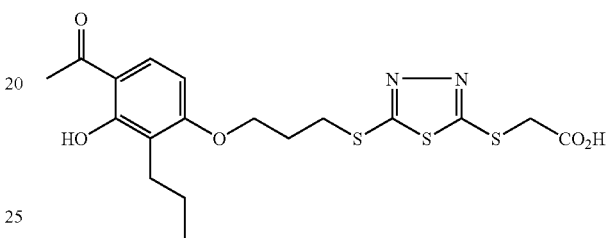

WO 92/10468 describes that GW-2433 is employable for prevention and treatment of atherosclerosis.

WO 97/28115 describes that L-165041 is employable for treatment of diabetes and suppression of obesity.

WO 99/04815 describes that YM-16638 shows effects for reducing serum cholesterol and reducing LDL cholesterol.

Recently, JBC, 272(6), p 3406–3410, 1997 and Cell, 99, p 335–345, 1999 describe proposal for application of PPAR δ ligand as an anti-cancer agent and an anti-inflammatory agent.

The above-mentioned GW-2433 and L-165041 are substituted phenoxyacetic acid derivatives and YM-16638 is a substituted thiaziazole-thioacetic acid derivative. Thus, they are apparently different in their structure from the substituted phenylacetic acid derivative of the invention having the below-mentioned formula (II).

As the substituted phenylacetic acid derivatives, wo 9958510 describes the following compound A, WO 9946232 describes the following compound B, and EP 908454 and WO 9815274 describe the following compound C:

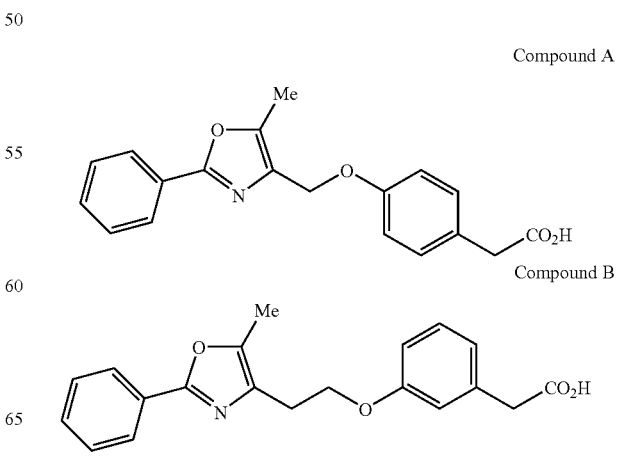

-continued

Compound C

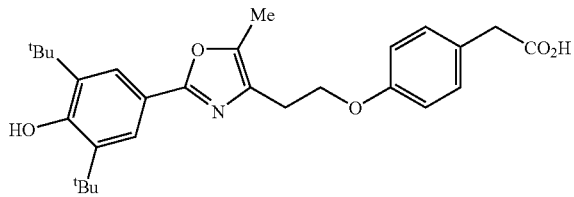

Each of the above-mentioned compounds A, B and C has a structure in which the oxazole ring connects to the phenylacetic acid via an alkylene chain having an oxygen atom, while the compound of the invention having the below-mentioned formula (II) has no such ether bonding between the oxazole ring and the phenylacetic acid.

DISCLOSURE OF THE INVENTION

The invention has an object to provide a compound having the following general formula (I) or (II), or a salt thereof, which has an activity of peroxisome proliferator-activated receptor.

In one aspect, the invention resides in a phenylacetic acid derivative having the following formula (I) or a salt thereof:

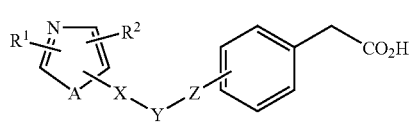

(I)

[wherein each of $R^1$ and $R^2$ independently is a hydrogen atom, a halogen atom, nitro, an alkyl group having 1–8 carbon atoms, an alkoxy group having 1–8 carbon atoms, an alkyl group having 1–8 carbon atoms which has 1 to 3 halogen substituents, an alkoxy group having 1–8 carbon atoms which has 1 to 3 halogen substituents, an alkenyl group having 2–8 carbon atoms, an alkynyl group having 2–8 carbon atoms, a 3–7 membered cycloalkyl group, an alkyl group having 1–8 carbon atom which has a 3–7 membered cycloalkyl substituent, an aryl group having 6–10 carbon atoms which optionally has a substituent, an arylalkyl group which has a $C_{6-10}$ aryl portion and $C_{1-8}$ alkyl portion, a heterocyclic group which optionally has a substituent or a heterocyclic-alkyl group having an alkyl group of 1–8 carbon atoms;

A is an oxygen atom, a sulfur atom, or $NR^3$ in which $R^3$ is a hydrogen atom or an alkyl group having 1–8 carbon atoms;

each of X and Z independently is —C(=O)—, —C(=O)NH—, —C(=N—OR$^4$)—, —CH(OR$^5$)—, —NH(C=O)—, —NHSO$_2$—, —SO$_2$NH—, —CH=CH—, —C≡C—, or a bond in which each of $R^4$ and $R^5$ is a hydrogen atom or an alkyl group having 1–8 carbon atoms; and Y is an alkylene chain having 1–8 carbon atoms].

In another aspect, the invention resides in a phenylacetic acid derivative having the following formula (II) or a salt thereof:

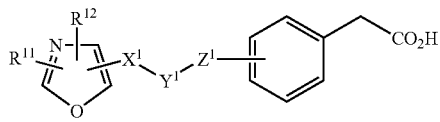

(II)

[wherein each of $R^{11}$ and $R^{12}$ independently is a hydrogen atom, a halogen atom, nitro, hydroxyl, amino, an alkyl group having 1–8 carbon atoms, an alkoxy group having 1–8 carbon atoms, an alkyl group having 1–8 carbon atoms which has 1 to 3 halogen substituents, an alkoxy group having 1–8 carbon atoms which has 1 to 3 halogen substituents, an alkenyl group having 2–8 carbon atoms, an alkynyl group having 2–8 carbon atoms, a 3–7 membered cycloalkyl group, an alkyl group having 1–8 carbon atoms which has a 3–7 membered cycloalkyl substituent, or a phenyl, naphthyl, benzyl, phenethyl, pyridyl, thienyl, furyl, quinolyl, or benzothienyl group which optionally has a substituent selected from the group consisting of a halogen atom, nitro, hydroxyl, amino, an alkyl group having 1–8 carbon atoms, an alkoxy group having 1–8 carbon atoms, an alkyl group having 1–8 carbon atoms which has 1 to 3 halogen substituents, an alkoxy group having 1–8 carbon atoms which has 1 to 3 halogen substituents, an alkenyl group having 2–8 carbon atoms, an alkynyl group having 2–8 carbon atoms, a 3–7 membered cycloalkyl group, an alkyl group having 1–8 carbon atoms which has a 3–7 membered cycloalkyl substituent, phenyl and pyridyl;

each of $X^1$ and $Z^1$ independently is —C(=O)—, —C(=O)NH—, —C(=N—OR$^{14}$)—, —CH(OR$^{15}$)—, —NH(C=O)—, —NHSO$_2$—, —SO$_2$NH—, —CH=CH—, —C≡C—, or a bond in which each of $R^{14}$ and $R^{15}$ is a hydrogen atom or an alkyl group having 1–8 carbon atoms; and $Y^1$ is an alkylene chain having 1–8 carbon atoms].

Further, the invention resides in an activator of peroxisome proliferator activated receptor which contains as an effective component a phenylacetic acid derivative of the formula (I) or a phenylacetic acid derivative of the formula (II) or their salts.

The present invention is described below in more detail.

The meanings of the symbols in the formula (I) are described below.

The halogen atom for $R^1$ and $R^2$ of the formula (I) can be fluorine, chlorine, or bromine.

The alkyl groups having 1–8 carbon atoms for $R^1$, $R^2$, $R^3$, $R^4$ and $R^5$ can be methyl, ethyl, propyl, isopropyl, butyl, isobutyl, t-butyl, or pentyl.

The alkoxy group having 1–8 carbon atoms for $R^1$ and $R^2$ can be methoxy, ethoxy, propyloxy, isopropyloxy, butyloxy, isobutyloxy, t-butyloxy, or pentyloxy.

The alkyl group having 1–8 carbon atoms which has 1–3 halogen substituents for $R^1$ and $R^2$ can be chloromethyl, fluoromethyl, bromomethyl, 2-chloroethyl, 2-fluoroethyl, or trifluoromethyl.

The alkoxy group having 1–8 carbon atoms which has 1–3 halogen substituents for $R^1$ and $R^2$ can be chloromethoxy, fluoromethoxy, bromomethoxy, 2-chloroethoxy, 2-fluoroethoxy, or trifluoroethoxy.

The alkenyl group having 2–8 carbon atoms for $R^1$ and $R^2$ can be vinyl or allyl. The alkynyl group having 2–8 carbon atoms can be propargyl. The cycloalkyl group having 3–7 carbon atoms can be cyclohexyl or cyclopentyl. The alkyl group having a 3–7 membered cycloalkyl substituent can be cyclohexylmethyl or cyclopentylmethyl.

The aryl group for the aryl group optionally having a substituent for $R^1$ and $R^2$ can be phenyl or naphthyl.

The arylalkyl group for the arylalkyl group (which has an aryl moiety of 6–10 carbon atoms and an alkyl moiety of 1–8 carbon atoms) optionally having a substituent can be benzyl or phenethyl.

The heterocyclic group for the heterocyclic group optionally having a substituent can be a 5–7 membered cyclic group having ring-forming 1–4 hetero atoms such as nitrogen, oxygen and sulfur. For instance, pyridyl, thienyl and furyl can be mentioned. Further, a benzene ring condensed with the heterocyclic group such as quinolyl or benzothienyl can be mentioned.

The heterocyclic group for the heterocyclic ring-alkyl group (the alkyl moiety has 1–8 carbon atoms) optionally having a substituent can be the same as that described hereinbefore for the heterocyclic group optionally having a substituent. The alkyl group preferably has 1–3 carbon atoms.

The substituent for the substituents of the aryl group optionally having a substituent, the arylalkyl group (the aryl moiety has 6–10 carbon atoms, and the alkyl moiety has 1–8 carbon atoms) optionally having a substituent, the heterocyclic group optionally having a substituent, and a heterocyclic ring-alkyl group (the alkyl moiety has 1–8 carbon atoms) optionally having a substituent can be a halogen atom such as chlorine, bromine, or fluorine, nitro, hydroxyl, amino, an alkyl amino group having 1–8 carbon atoms such as methylamino, or ethylamino, a dialkylamino group having 2–10 carbon atoms such as dimethylamino, an alkyl group having 1–8 carbon atoms such as methyl, ethyl, propyl, isopropyl, or butyl, an alkoxy group having 1–8 carbon atoms such as methoxy, ethoxy, propoxy, isopropoxy, or butoxy, an alkyl group having 1–8 carbon atoms which has 1–3 halogen substituents such as chloromethyl, fluoromethyl, bromomethyl, 2-chloroethyl, 2-fluoroethyl, or trifluoromethyl, an alkoxy group having 1–8 carbon atoms which has 1–3 halogen substituents such as chloromethoxy, fluoromethoxy, bromomethoxy, 2-chloroethoxy, 2-fluoroethoxy, or trifluoromethoxy, an alkyenyl group having 2–8 carbon atoms such as vinyl or allyl, an alkynyl group having 2–8 carbon atoms such as propargyl, a cycloalkyl group having 3–7 carbon atoms such as cyclohexyl or cyclopentyl, an alkyl group having a cycloalkyl group of 3–7 carbon atoms such as cyclohexylmethyl or cyclopentylmethyl, phenyl, or pyridyl.

The meanings of the symbols in the formula (II) are described below.

The halogen atom, alkoxy groups having 1–8 carbon atoms, alkyl group having 1–8 carbon atoms which has 1–3 halogen substituents, alkoxy group having 1–8 carbon atoms which has 1–3 halogen substituents, alkenyl group having 2–8 carbon atoms, alkynyl group having 2–8 carbon atoms, cycloalkyl group having 3–7 carbon atoms, alkyl group having 1–8 carbon atoms which has a cycloalkyl group of 3–7 carbon atoms for $R^{11}$ and $R^{12}$ of the formula (II) can be those described for the halogen atom, alkoxy group, alkyl group having 1–8 carbon atoms which has a halogen substituent, alkoxy group having 1–8 carbon atoms which has a halogen substituent, alkenyl, alkynyl, cycloalkyl group, and alkyl group having 1–8 carbon atoms which has a cycloalkyl group of 3–7 carbon atoms for $R^1$ and $R^2$ of the formula (I).

The alkyl group having 1–8 carbon atoms for $R^{11}$, $R^{12}$, $R^{14}$, and $R^{15}$ of the formula (II) can be an alkyl group described for $R^1$, $R^2$, $R^3$, $R^4$ and $R^5$.

In the case that $R^{11}$ or $R^{12}$ of the formula (II) is phenyl, naphthyl, benzyl, phenethyl, pyridyl, thienyl, furyl, quinolyl, or benzothienyl, these rings may have such substituents as a halogen atom such as chlorine, bromine, or fluorine, nitro, hydroxyl, amino, an alkyl amino group having 1–8 carbon atoms such as methylamino, or ethylamino, a dialkylamino group having 2–10 carbon atoms such as dimethylamino, an alkyl group having 1–8 carbon atoms such as methyl, ethyl, propyl, isopropyl, or butyl, an alkoxy group having 1–8 carbon atoms such as methoxy, ethoxy, propoxy, isopropoxy, or butoxy, an alkyl group having 1–8 carbon atoms which has 1–3 halogen substituents such as chloromethyl, fluoromethyl, bromomethyl, 2-chloroethyl, 2-fluoroethyl, or trifluoromethyl, an alkoxy group having 1–8 carbon atoms which has 1–3 halogen substituents such as chloromethoxy, fluoromethoxy, bromomethoxy, 2-chloroethoxy, 2-fluoroethoxy, or trifluoromethoxy, an alkyenyl group having 2–8 carbon atoms such as vinyl or allyl, an alkynyl group having 2–8 carbon atoms such as propargyl, a cycloalkyl group having 3–7 carbon atoms such as cyclohexyl or cyclopentyl, an alkyl group having a cycloalkyl group of 3–7 carbon atoms such as cyclohexylmethyl or cyclopentylmethyl, phenyl, or pyridyl.

(1) It is preferred that the compound of the invention is a phenylacetic acid derivative of the formula (II) in which —$X^1$—$Y^1$-$Z^1$- is bonded to the 3- or 4-position of the phenylacetic acid or a salt thereof.

(2) It is also preferred that the compound of the invention is a phenylacetic acid derivative of the formula (II) or a phenylacetic acid derivative of (1) above in which $X^1$ is a bond, and $Z^1$ is —C(=O)—, or a salt thereof.

(3) It is also preferred that the compound of the invention is a phenylacetic acid derivative of the formula (II) or a phenylacetic acid derivative of (1) or (2) above in which —$X^1$—$Y^1$-$Z^1$- is bonded to the 4-position of the oxazole ring, or a salt thereof.

(4) It is also preferred that the compound of the invention is a phenylacetic acid derivative of the formula (II) or a phenylacetic acid derivative of one of (1) to (3) above in which $R^{11}$ is a phenyl or naphthyl group which optionally has a substituent selected from the group consisting chlorine, fluorine, hydroxyl, an alkyl group having 1–5 carbon atoms, and an alkyl group having 1–5 carbon atoms, and it is bonded to the 2-position of the oxazole ring, or a salt thereof.

(5) It is also preferred that the compound of the invention is a phenylacetic acid derivative of the formula (II) or a phenylacetic acid derivative of one of (1) to (4) above in which $R^{12}$ is an alkyl group having 3–6 carbon atoms, and it is bonded to the 5-position of the oxazole ring, or a salt thereof.

The compound of the invention, that is a phenylacetic acid of the formula (I), a phenylacetic acid of the formula (II), or a salt thereof, can be a stereoisomer such as cis or trans, or an optical isomer. These isomers are included in the invention.

The compound of the invention includes a pharmaceutically acceptable salt such as an alkali metal salt, e.g., sodium salt or potassium salt.

The compound of the formula (I) according to the invention can be prepared by the following synthesis methods.

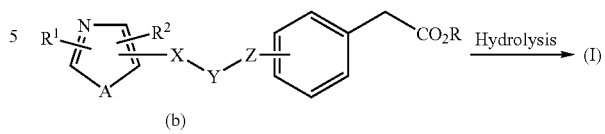

[In the formula, R is a lower alkyl group, and $R^1$, $R^2$, A, X, Y and Z are the same as above]

A phenylacetic acid derivative of the formula (I) also can be prepared by hydrolyzing a phenylacettic acid ester of the formula (b) in a solvent such as water in the presence of sodium hydroxide or potassium hydroxide.

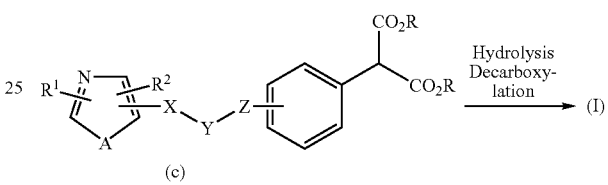

[In the formula, R is a lower alkyl group, and $R^1$, $R^2$, A, X, Y and Z are the same as above]

A phenylacetic acid derivative of the formula (I) also can be prepared by hydrolysis and decarboxylation comprising heating a malonate ester of the formula (c) in a solvent in the presence of a basic compound.

The compounds of the formulas (a), (b), and (c) which are the starting compounds in the synthesis methods 1–3 can be prepared by the following synthesis methods.

[Synthesis 1 of the Starting Compound]

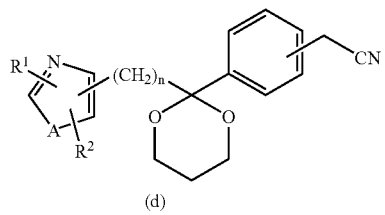

[In the formula, $R^1$, $R^2$, A, X, Y and Z are the same as above]

A phenylacetic acid derivative of the formula (I) can be prepared by hydrolysis comprising heating an acetonitrile compound of the formula (a) in a solvent such as water in the presence of an acid catalyst such as sulfuric acid.

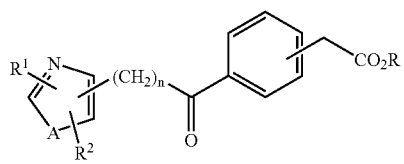

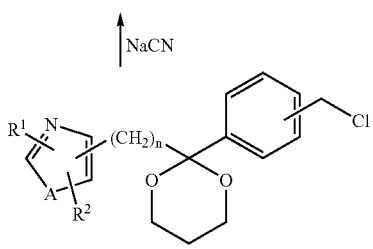

-continued
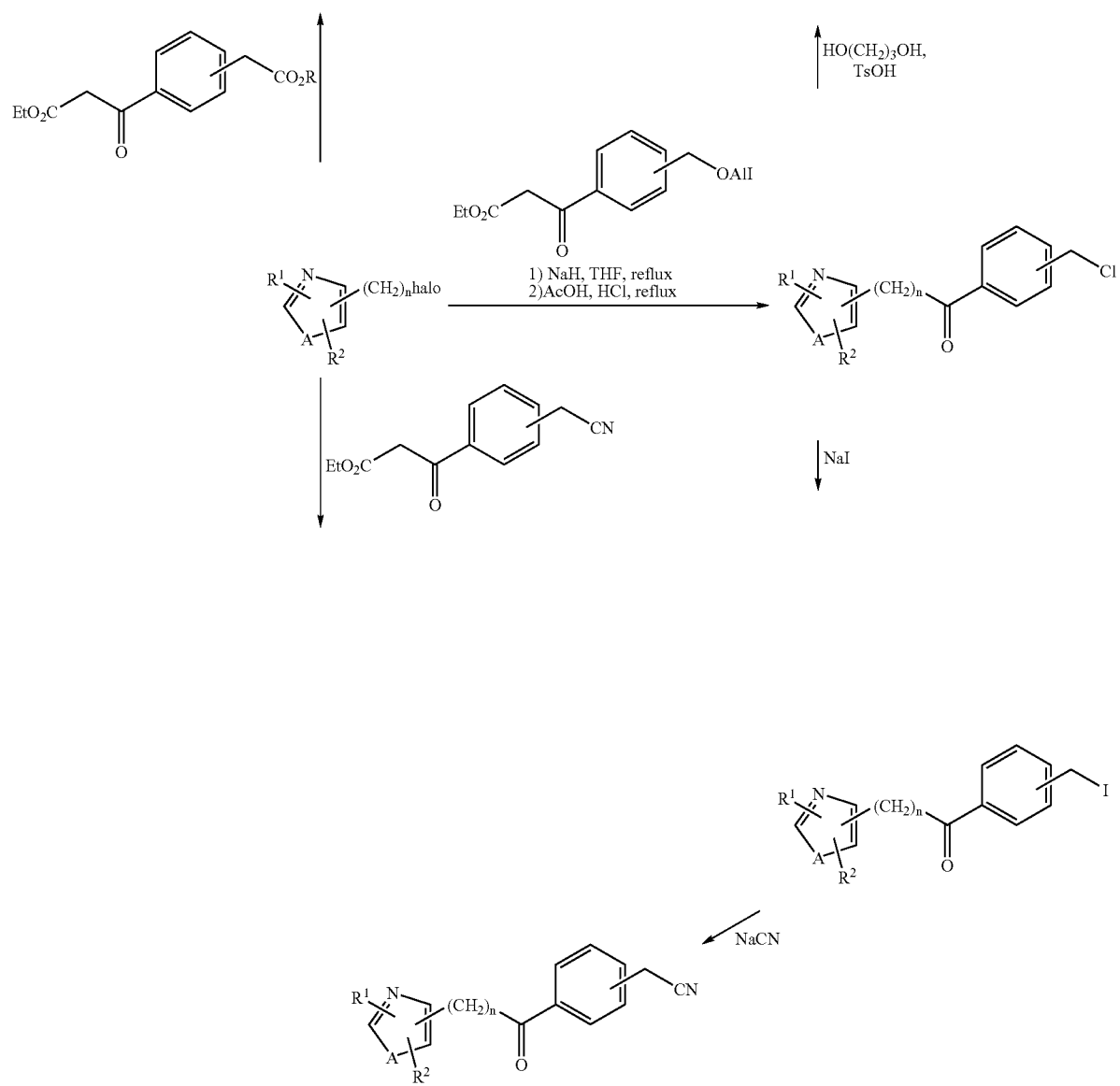

[In the formula, halo is a halogen atom, All is allyl, Ts is tosyl, R is a lower-alkyl group, n is an integer of 1–8, and $R^1$, $R^2$, and A are the same as above]
The protecting propanedioxy group of the acetonitrile compound of the formula (d) can be converted into —(C=O)— group for Z by hydrolysis.
[Synthesis 2 of the Starting Compound]
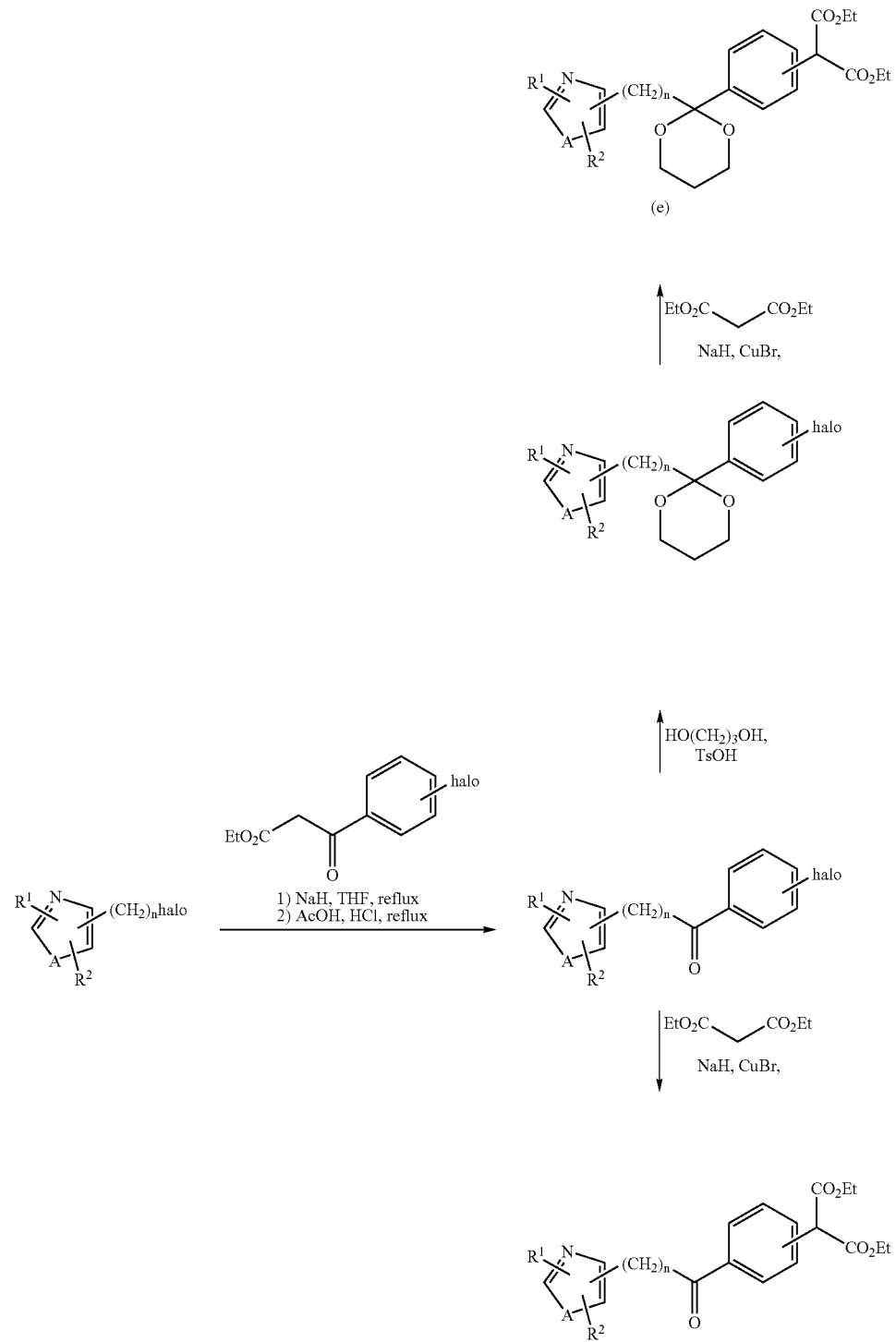

[In the formula, halo is a halogen atom, n is an integer of 1–8, and $R^1$, $R^2$, and A are the same as above]

The protecting propanedioxy group of the malonate ester compound of the formula (e) can be converted into —(C=O)— group for Z by hydrolysis.

[Synthesis 3 of the Starting Compound]

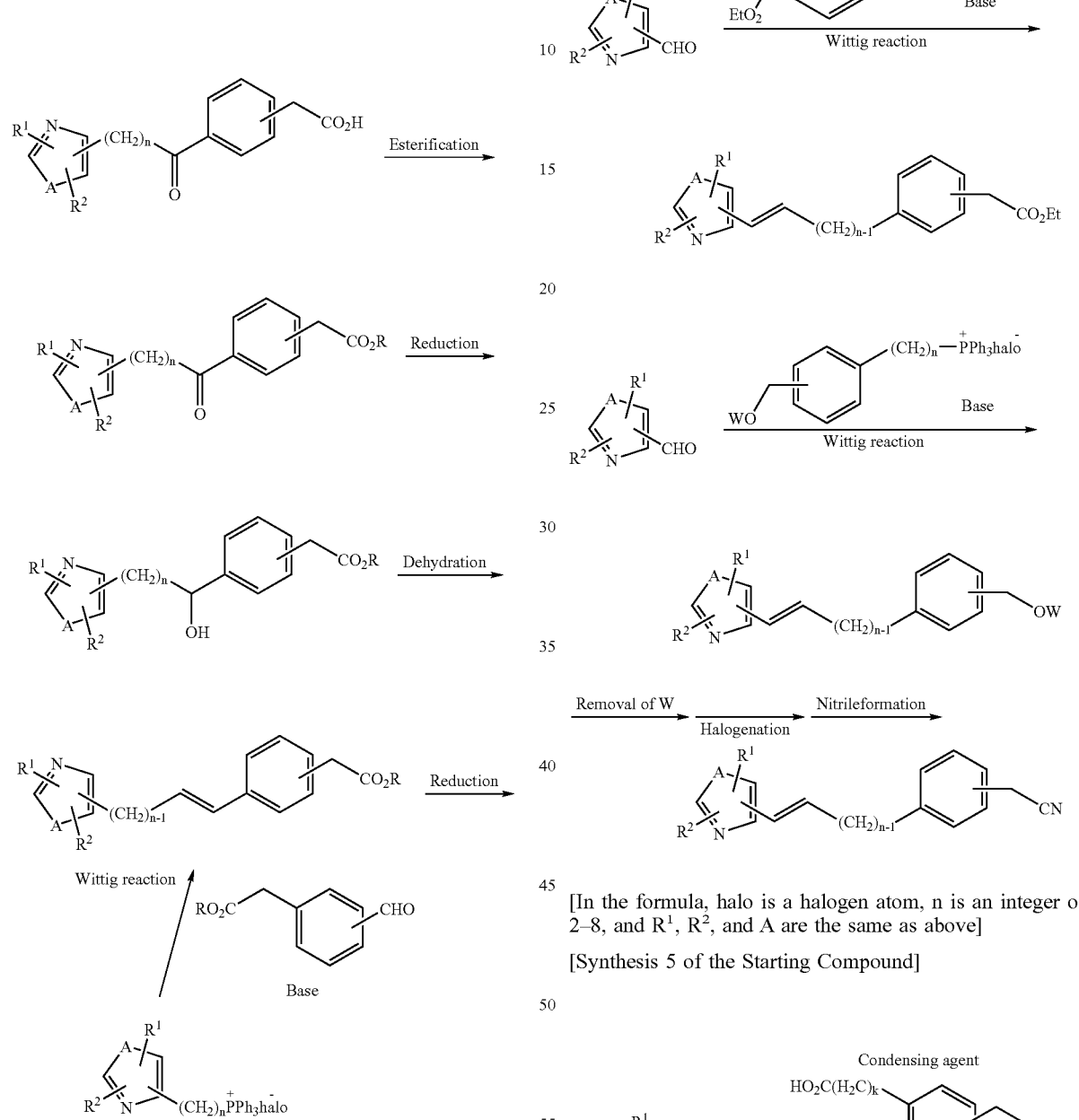

[In the formula, R is a lower alkyl group, halo is a halogen atom, n is an integer of 1–8, and $R^1$, $R^2$, and A are the same as above]

[Synthesis 4 of the Starting Compound]

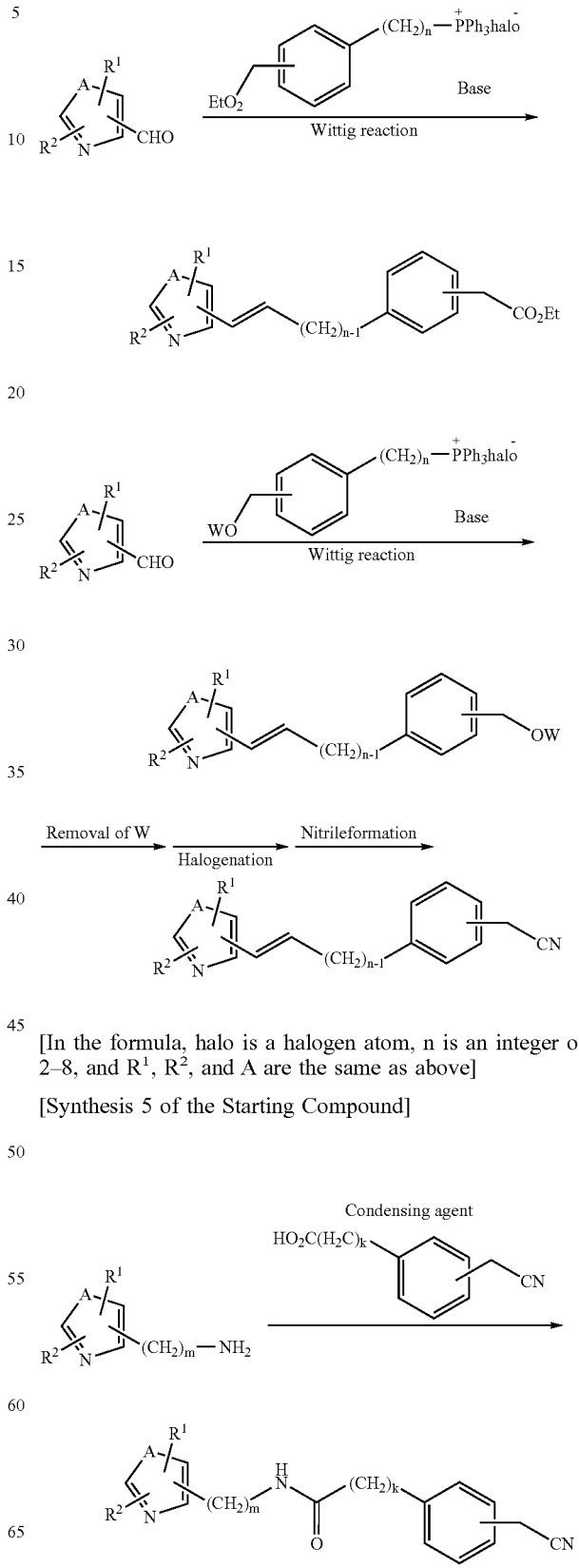

[In the formula, halo is a halogen atom, n is an integer of 2–8, and $R^1$, $R^2$, and A are the same as above]

[Synthesis 5 of the Starting Compound]

-continued

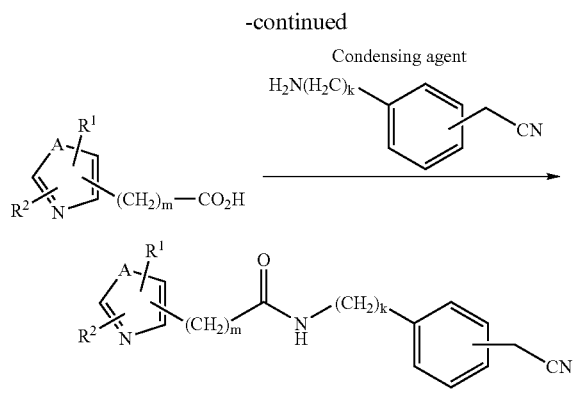

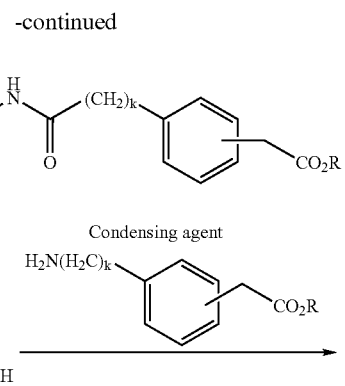

[in the formula, each of m and k is 0 to 4, and $R^1$, $R^2$, and A are the same as above]

[Synthesis 6 of the Starting Compound]

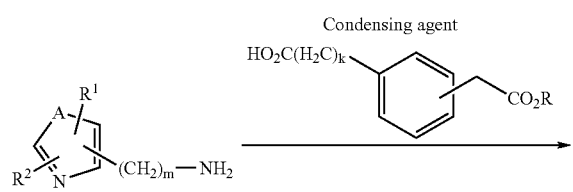

[in the formula, each of m and k is 0 to 4, and $R^1$, $R^2$, and A are the same as above]

The representative compounds according to the invention are described below.

[Examples of the Compounds of the Formula (I) in which —X—Y-Z- is Bonded to the 4-Position, $R^1$ is Bonded to the 2-Position, and $R^2$ is Bonded to the 5-Position]

TABLE

| $R^1$ | $R^2$ | A | X | Y | Z |
|---|---|---|---|---|---|
| (2,3-Cl)phenyl | propyl | S | bond | $(CH_2)_3$ | C=O(4) |
| (2,3-Cl)phenyl | hexyl | NH | bond | $(CH_2)_3$ | C=O(4) |
| (2,4-Me)phenyl | propyl | O | bond | $(CH_2)_3$ | C=O(4) |
| (2,4-Me)phenyl | hexyl | NH | bond | $(CH_2)_5$ | C=O(4) |
| (2,4-Me)phenyl | isobutyl | NMe | bond | $(CH_2)_4$ | C=O(3) |
| (2-Cl)phenyl | propyl | S | bond | $(CH_2)_4$ | C=O(4) |
| (2-Cl)phenyl | hexyl | S | bond | $(CH_2)_5$ | C=O(4) |
| (2-Cl)phenyl | isopropyl | NMe | bond | $(CH_2)_3$ | C=O(3) |
| (2-Cl)phenyl | isopropyl | O | bond | $(CH_2)_4$ | C=O(3) |
| (2-Cl)phenyl | isopropyl | S | bond | $(CH_2)_5$ | C=O(3) |
| (2-Me)phenyl | isopropyl | NH | bond | $(CH_2)_3$ | C=O(4) |
| (2-Me)phenyl | isobutyl | NMe | bond | $(CH_2)_4$ | C=O(4) |
| (2-Me)phenyl | propyl | O | bond | $(CH_2)_5$ | C=O(4) |
| (2-Me)phenyl | isopropyl | O | bond | $(CH_2)_3$ | C=O(3) |
| (2-Me)phenyl | isobutyl | NMe | bond | $(CH_2)_4$ | C=O(3) |
| (2-Me,4-OMe)phenyl | isopropyl | NMe | bond | $(CH_2)_4$ | C=O(4) |
| (2-Me,4-OMe)phenyl | isobutyl | O | bond | $(CH_2)_5$ | C=O(4) |
| (2-Me,4-OMe)phenyl | propyl | O | bond | $(CH_2)_3$ | C=O(3) |
| (2-Me,4-OMe)phenyl | hexyl | S | bond | $(CH_2)_4$ | C=O(3) |
| (2-OH)phenyl | isopropyl | S | bond | $(CH_2)_3$ | C=O(4) |
| (2-OH)phenyl | isobutyl | O | bond | $(CH_2)_4$ | C=O(4) |
| (2-OH)phenyl | isobutyl | O | bond | $(CH_2)_3$ | C=O(3) |
| (2-OH,4-OMe)phenyl | propyl | S | bond | $(CH_2)_5$ | C=O(4) |
| (2-OH,4-OMe)phenyl | hexyl | S | bond | $(CH_2)_4$ | C=O(4) |
| (4-Bn)phenyl | hexyl | O | bond | $(CH_2)_3$ | C=O(4) |
| (4-Bn)phenyl | propyl | S | bond | $(CH_2)_4$ | C=O(3) |
| (4-Bz)phenyl | isopropyl | O | bond | $(CH_2)_3$ | C=O(4) |

TABLE-continued

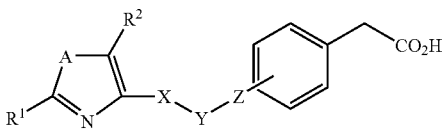

| R¹ | R² | A | X | Y | Z |
|---|---|---|---|---|---|
| (4-Bz)phenyl | hexyl | O | bond | $(CH_2)_5$ | C=O(3) |
| (4-$CF_3$)phenyl | isopropyl | NMe | bond | $(CH_2)_3$ | C=O(4) |
| (4-$CF_3$)phenyl | isobutyl | O | bond | $(CH_2)_3$ | C=O(4) |
| (4-$CF_3$)phenyl | hexyl | O | bond | $(CH_2)_4$ | C=O(3) |
| (4-Cl)phenyl | propyl | S | bond | $(CH_2)_2$ | C=O(3) |
| (4-$OCF_3$)phenyl | isobutyl | S | bond | $(CH_2)_3$ | C=O(4) |
| (4-$OCF_3$)phenyl | isopropyl | NH | bond | $(CH_2)_3$ | C=O(3) |
| (4-OPh)phenyl | propyl | S | bond | $(CH_2)_3$ | C=O(4) |
| (4-OPh)phenyl | isobutyl | S | bond | $(CH_2)_3$ | C=O(3) |
| 1-naphthyl | cyclopropylmethyl | O | bond | $(CH_2)_4$ | C=O(4) |
| 2-imidazolyl | 2-pyridylmethyl | S | bond | $(CH_2)_4$ | C=O(4) |
| 2-indolyl | isopropyl | S | bond | $(CH_2)_5$ | C=O(4) |
| 2-thienyl | 2-phenylethyl | O | bond | $(CH_2)_5$ | C=O(4) |
| 2-naphthyl | benzyl | O | bond | $(CH_2)_4$ | C=O(4) |
| 2-furanyl | vinyl | S | bond | $(CH_2)_3$ | C=O(4) |
| 2-benzimidaolyl | isopropyl | NH | bond | $(CH_2)_4$ | C=O(4) |
| 2-benzimidazolyl | isopropyl | O | bond | $(CH_2)_4$ | C=O(3) |
| 2-benzothienyl | isopropyl | NH | bond | $(CH_2)_3$ | C=O(4) |
| 2-benzothienyl | hexyl | S | bond | $(CH_2)_3$ | C=O(3) |
| (2,4-Cl)phenyl | hexyl | NMe | CH(OH) | $(CH_2)_3$ | bond(4) |
| (2,4-Cl)phenyl | isopropyl | S | bond | $(CH_2)_4$ | bond(4) |
| (2,4-Cl)phenyl | isopropyl | S | CH=CH | $(CH_2)_2$ | bond(3) |
| (2,4-Me)phenyl | isopropyl | O | bond | $(CH_2)_3$ | NHC=O(4) |
| (2,4-Me)phenyl | isobutyl | O | NH | $(CH_2)_4$ | bond(4) |
| (2,4-Me)phenyl | propyl | O | NHCO | $(CH_2)_3$ | bond(4) |
| (2,4-Me)phenyl | isobutyl | S | NH | $(CH_2)_4$ | bond(3) |
| (2,4-Me)phenyl | propyl | NH | NHCO | $(CH_2)_5$ | bond(3) |
| (2-Cl)phenyl | hexyl | O | bond | $(CH_2)_5$ | CH=CH(4) |
| (2-Cl)phenyl | propyl | NH | CH=CH | $(CH_2)_4$ | bond(3) |
| (2-Cl)phenyl | hexyl | O | bond | $(CH_2)_5$ | CH=CH(3) |
| (2-Me)phenyl | isopropyl | S | bond | $(CH_2)_3$ | NHC=O(4) |
| (2-Me)phenyl | isobutyl | S | NH | $(CH_2)_4$ | bond(4) |
| (2-Me)phenyl | isopropyl | O | bond | $(CH_2)_3$ | NHC=O(3) |
| (2-Me)phenyl | isobutyl | O | NH | $(CH_2)_4$ | bond(3) |
| (2,4-Cl)phenyl | hexyl | NMe | CH(OH) | $(CH_2)_3$ | bond(4) |
| (2-Me,4-OMe)phenyl | isobutyl | O | bond | $(CH_2)_3$ | NHC=O(4) |
| (2-OH)phenyl | isopropyl | NH | CONH | $(CH_2)_3$ | bond(4) |
| (2-OH,4-Cl)phenyl | isopropyl | O | CONH | $(CH_2)_3$ | bond(4) |
| (2-OH,4-Cl)phenyl | isopropyl | O | CONH | $(CH_2)_3$ | bond(3) |
| (2-OH,4-Me)phenyl | propyl | S | NH | $(CH_2)_4$ | bond(4) |
| 1-naphthyl | ethyl | O | bond | $(CH_2)_4$ | bond(3) |
| 2-imidazolyl | 2-phenylethyl | O | CH(OH) | $(CH_2)_3$ | bond(3) |
| 2-indolyl | 2-pyridylmethyl | O | bond | $(CH_2)_5$ | CH=CH(3) |
| 2-thienyl | cyclopropylmethyl | S | bond | $(CH_2)_3$ | bond(3) |
| 2-naphthyl | isopropyl | O | CONH | $(CH_2)_3$ | CH=CH(3) |
| 2-furanyl | benzyl | S | CH(OH) | $(CH_2)_3$ | bond(3) |
| 2-benzimidazolyl | isopropyl | NMe | NH | $(CH_2)_4$ | bond(4) |
| 2-benzothienyl | isopropyl | S | bond | $(CH_2)_3$ | NHC=O(4) |

Remark: Numeral in ( ) means a position where Z is substituted.

The pharmacological effects of the invention are described below.

The PPARδ activating effect of the compound of the invention was determined by the following method:

A chimeric receptor expression plasmid (GAL4-hPPARδ LBD), a reporter plasmid (UASx4-TK-LUC) and β-galactosidase (β-GAL) are transfected into CV-1 cells by utilizing a lipofection reagent DMRIE-C (Life Technologies). Subsequently, it is incubated for 40 hours in the presence of a compound of the invention or a compound for comparison (GW-2433), and then the luciferase activity and β-GAL activity are measured on the soluble cells.

The luciferase activity is calibrated by the β-GAL activity. A relative ligand activity relating to PPARγ-activating effect is calculated in the same manner (see the below-described Example 3).

As is described in Example 3, the phenylacetic acid derivative of the invention (Example 1) shows excellent PPAR activating effect (PPARγ or δ activating effect).

Since the phenylacetic acid derivative of the formula (I) or (II) or its salt according to the invention shows excellent PPAR activating effect, it is expected to serve as remedy for prevention and treatment of the following diseases: hyperglycemia, hyperlipidemia, obesity, syndrome X, hyperchloresterolemia, hyperlipopreoteinemia, other dysbolismic diseases, hiperlipemia, arterial sclerosis, diseases of cardiovascular systems, hyperphagia, ischemic diseases, malignant tumors such as lung cancer, mammary cancer, colonic cancer, cancer of great intestine, and ovary cancer, Alzheimer's disease, inflammatory disease, osteoporosis (Mano H. et al., (2000) J. Biol. Chem., 175:8126–8132), Basedow's disease, adrenal cortical dystrophy, multiple sclerosis, and demyelinating neuropathy.

The compound of the invention can be administered to human beings by ordinary administration methods such as oral administration or parenteral administration.

The compound can be granulated in ordinary manners for the preparation of pharmaceuticals. For instance, the compound can be processed to give pellets, granule, powder, capsule, suspension, injection, suppository, and the like.

For the preparation of these pharmaceuticals, ordinary additives such as vehicles, disintegrators, binders, lubricants, dyes, and diluents. As the vehicles, lactose, D-mannitol, crystalline cellulose and glucose can be mentioned. Further, there can be mentioned starch and carboxymethylcellulose calcium (CMC-Ca) as the disintegrators, magnesium stearate and talc as the lubricants, and hydroxypropylcellulose (HPC), gelatin and polyvinylpirrolidone (PVP) as the binders.

The compound of the invention can be administered to an adult generally in an amount of 0.1 mg to 100 mg a day by parenteral administration and 1 mg to 2,000 mg a day by oral administration. The dosage can be adjusted in consideration of age and conditions of the patient.

The invention is further described by the following non-limiting examples.

EXAMPLE 1

[4-[4-[2-(2-Chlorophenyl)-5-isopropyloxazol-4-yl]butyryl]phenyl]acetic acid (1) [2-(2-Chlorophenyl)-5-isopropyloxazol-4-yl]acetonitrile In acetone (2 mL) was dissolved 2-(2-chlorophenyl)-4-iodomethyl-5-isopropyloxazole (590 mg, 1.63 mmol). Sodium cyanide (88 mg, 1.63 mmol) was added, and the resulting mixture was heated under reflux for 22 hours. The reaction mixture was cooled to room temperature, poured into water, and extracted with ethyl acetate. The organic layer was washed successively with water and a saturated brine, dried over sodium sulfate, filtered and concentrated. The resulting residue was purified by flash column chromatography on silica gel (hexane/ethyl acetate=5/1), to obtain the desired compound (37 mg, 82%).

$^1$H NMR (CDCl$_3$, 400 MHz) δ: 1.37 (d, 6H, J=7 Hz), 3.22 (m, 1H), 3.70 (s, 2H), 7.3–7.4 (m, 2H), 7.4–7.5 (m, 1H), 7.9–8.0 (m, 1H)

(2) [2-(2-Chlorophenyl)-5-isopropyloxazol-4-yl]acetic acid

In a mixture of conc. sulfuric acid (2 mL) and water (1 mL) was suspended [2-(2-chlorophenyl)-5-isopropyloxazol-4-yl]acetonitrile (346 mg, 1.33 mmol). The suspension was stirred at 100° C. for 2 hours. The reaction mixture was cooled to room temperature and poured into an ice-water mixture, and extracted three times with chloroform. The organic layer was successively washed with water and saturated brine, dried over sodium sulfate, filtered, and concentrated, to obtain the desired compound (393 mg).

$^1$H NMR (CDCl$_3$, 400 MHz) δ: 1.34 (d, 6H, J=7 Hz), 3.10 (m, 1H), 3.68 (s, 2H), 7.3–7.4 (m, 2H), 7.4–7.6 (m, 1H), 7.9–8.0 (m, 1H)

(3) 2-[2-(2-Chlorophenyl)-5-isopropyloxazol-4-yl]ethanol

In tetrahydrofuran (3 mL) was suspended lithium aluminum hydride (107 mg, 2.81 mmol). Under cooling with ice, too the suspension was dropwise added a solution of [2-(2-chlorophenyl)-5-isopropyloxazol-4-yl]acettic acid (393 mg, 1.40 mmol) in tetrahydrofuran (3 mL) for 5 min. The resulting mixture was allowed to reach room temperature, stirred for 2 hours, diluted with ether (15 mL), and quenched with saturated sodium sulfate. Insolubles were filtered off. The filtrate was dried over sodium sulfate, filtered, and concentrated, to obtain the desired compound (235 mg, 63%).

$^1$H NMR (CDCl$_3$, 400 MHz) δ: 1.32 (d, 6H, J=6 Hz), 2.78 (t, 2H, J=6 Hz), 3.09 (m, 1H), 3.45 (t, 1H, J=6 Hz), 3.94 (dt, 2H, J=6 Hz, 6 Hz), 7.3–7.5 (m, 3H), 7.9–8.0 (m, 1H)

(4) 2-(2-Chlorophenyl)-5-isopropyl-4-[2-(p-toluenesulfonyloxy)ethyl]oxazole

In a mixture of methylene chloride (1 mL) and pyridine (2 mL) was dissolved 2-[2-(2-chlorophenyl)-5-isopropyloxazol-4-yl]ethanol (159 mg, 0.598 mmol). Under cooling with water, to the solution was added p-toluenesulfonyl chloride (125 mg, 0.658 mmol). The mixture was stirred for 5 hours. The reaction mixture was poured into 1N HCl and extracted with chloroform. The organic layer was successively washed with water, saturated aqueous sodium hydrogen carbonate and saturated brine, dried over sodium sulfate, filtered, and concentrated. The residue was purified by flash chromatography on silica gel (hexane/ethyl acetate=2/1), to obtain the desired compound (123 mg, 49%).

$^1$H NMR (CDCl$_3$, 400 MHz) δ: 1.30 (d, 6H, J=7 Hz), 2.28 (s, 3H), 2.89 (t, 2H, J=7 Hz), 3.06 (m, 1H), 4.31 (t, 2H, J=7 Hz), 7.22 (d, 2H, J=8 Hz), 7.3–7.4 (m, 2H), 7.4–7.5 (m, 1H), 7.69 (d, 2H, J=8 Hz), 7.8–7.9 (m, 1H)

(5) 2-(2-Chlorophenyl)-4-(2-iodoethyl)-5-isopropyloxazole

In acetone (2 mL) was dissolved 2-(2-chlorophenyl)-5-isopropyl-4-[2-(p-toluenesulfonyloxy)ethyl]oxazole (123 mg, 0.293 mmol). To the solution was added sodium iodide (176 mg, 1.17 mmol). The mixture was heated overnight under reflux. The reaction mixture was allowed to reach room temperature, poured into water, and extracted with ethyl acetate. The organic layer was successively washed with water and saturated brine, dried over sodium sulfate, filtered, and concentrated, to obtain the desired compound (105 mg, 96%).

$^1$H NMR (CDCl$_3$, 400 MHz) δ: 1.35 (d, 6H, J=7 Hz), 3.0–3.2 (m, 3H), 3.46 (t, 2H, J=7 Hz), 7.3–7.5 (m, 3H), 7.9–8.0 (m, 1H)

(6) 1-[(4-Chloromethyl)phenyl]-4-[2-(2-chlorophenyl)-5-isopropyloxazol-4-yl]butan-1-one In tetrahydrofuran (1 mL) was suspended 60% sodium hydride (16 mg, 0.389 mg), and the resulting suspension was cooled with ice. To the cooled mixture was dropwise added a solution of ethyl 3-[(4-allyloxymethyl)phenyl]-3-oxopropionate (102 mg, 0.389 mmol) in tetrahydrofuran (2 mL) for 5 min. After 30 min., a solution of 2-(2-chlorophenyl)-4-(2-iodoethyl)-5-isopropyloxazole (146 mg, 0.389 mmol) in tetrahydrofuran (2 mL) was added, and the resulting mixture was heated for 21 hours under reflux. The reaction mixture was allowed to reach room temperature, poured into water, and extracted with ethyl acetate. The organic layer was successively washed with water and saturated brine, dried over sodium sulfate, filtered, and concentrated. The residue was purified by flash column chromatography on silica gel (hexane/ethyl acetate=3/1). To the obtained crude ethyl 2-[(4-allyloxymethyl)benzoyl]-4-[2-(2-chlorophenyl)-5-isopropyloxazol-4-yl]acetate were added acetic acid (1.5 mL) and conc. sulfuric acid (0.4 mL). The mixture was heated for 24 hours under reflux. The reaction mixture was allowed to reach room temperature, poured into a saturated sodium hydrogen carbonate solution, and extracted with ethyl acetate. The organic layer was successively washed with water and saturated brine, dried over sodium sulfate, filtered, and concentrated. The residue was purified by flash column chromatography on silica gel (hexane/ethyl acetate=3/1), to obtain the desired compound (49 mg, 30%).

$^1$H NMR (CDCl$_3$, 400 MHz) δ: 1.30 (d, 6H, J=7 Hz), 2.13 (m, 2H), 2.67 (t, 2H, J=7 Hz), 3.0–3.2 (m, 3H), 6.60 (s, 2H), 7.3–7.4 (m, 2H), 7.4–7.5 (m, 3H), 7.9–8.0 (m, 3H)

(7) 1-[(4-Iodomethyl)phenyl]-4-[2-(2-chlorophenyl)-5-isopropyloxazol-4-yl]butan-1-one In acetone (1 mL) was dissolved 1-[(4-chloromethyl)-phenyl]-4-[2-(2-chlorophenyl)-5-isopropyloxazol-4-yl]-butan-1-one (48 mg, 0.115 mmol). To the solution was added sodium iodide (35 mg, 0.231 mmol), and the resulting mixture was stirred overnight at room temperature. The reaction mixture was poured into water and extracted with ethyl acetate. The organic layer was successively washed with water and saturated brine, dried over sodium sulfate, filtered, and concentrated, to obtain the desired compound (58 mg, 100%).

$^1$H NMR (CDCl$_3$, 400 MHz) δ: 1.30 (d, 6H, J=7 Hz), 2.12 (m, 2H), 2.65 (t, 2H, J=7 Hz), 3.0–3.2 (m, 3H), 4.45 (s, 2H), 7.3–7.4 (m, 2H), 7.4–7.5 (m, 3H), 7.89 (d, 2H, J=8 Hz), 7.9–8.0 (m, 1H)

(8) [4-[4-[2-(2-Chlorophenyl)-5-isopropyloxazol-4-yl]butyryl]phenyl]acetonitrile In acetone (1.5 mL) was dissolved 1-[(4-iodomethyl)-phenyl]-4-[2-(2-chlorophenyl)-5-isopropyloxazol-4-yl]-butan-1-one (58 mg, 0.114 mmol). To the solution was added sodium cyanide (7 mg, 0.120 mmol), and the resulting mixture was heated overnight under reflux. The reaction mixture was allowed to reach room temperature, poured into water, and extracted with two portions of ethyl acetate. The organic layer was successively washed with water and saturated brine, dried over sodium sulfate, filtered and concentrated. The residue was purified by flash column chromatography on silica gel (hexane/ethyl acetate=2/1), to obtain the desired compound (3.2 mg, 7%).

$^1$H NMR (CDCl$_3$, 400 MHz) δ: 1.30 (d, 6H, J=7 Hz), 2.13 (m, 2H), 7.3–7.4 (m, 2H), 7.42 (t, 2H, J=8 Hz), 7.4–7.5 (m, 1H), 7.9–8.0 (m, 1H), 7.98 (d, 2H, J=8 Hz)

(9) [4-[4-[2-(2-Chlorophenyl)-5-isopropyloxazol-4-yl]-butyryl]phenyl]acetic acid In a mixture of conc. sulfuric acid and water (2/1, v/v, 0.5 mL) was suspended [4-[4-[2-(2-chlorophenyl)-5-isopropyloxazol-4-yl]butyryl]phenyl]acetonitrile (3.2 mg, 7.86 μmol). The suspension was stirred at 100° C. for 17 hours. The reaction mixture was allowed to reach room temperature, poured into an ice-water mixture, and extracted with chloroform. The organic layer was successively washed with water and saturated brine, dried over sodium sulfate, filtered, and concentrated. The residue was purified by preparative silica gel thin layer chromatography (chloroform/methanol=9/1), to obtain the desired compound (1.5 mg, 45%).

$^1$H NMR (CDCl$_3$, 400 MHz) δ: 1.30 (d, 6H, J=7 Hz), 2.10 (m, 2H), 2.65 (t, 2H, J=7 Hz), 3.03 (t, 2H, J=7 Hz), 3.0–3.2 (m, 1H), 3.70 (s, 2H), 7.3–7.4 (m, 2H), 7.37 (d, 2H, J=8 Hz), 7.4–7.5 (m, 1H), 7.9–8.0 (m, 3H)

EXAMPLE 2

[4-[3-[2-(2-Chlorophenyl)-5-isopropyloxazol-4-yl]propionyl]phenyl]acetic acid (1) 1-[(4-Chloromethyl)phenyl]-3-[2-(2-chlorophenyl)-5-isopropyloxazol-4-yl]propan-1-one In tetrahydrofuran (3 mL) was suspended 60% sodium hydride (40 mg, 1.00 mmol). The suspension was cooled with ice. To the cooled suspension was dropwise added a solution of ethyl 3-[(4-allyloxymethyl)phenyl]-3-oxopropanoate (262 mg, 1.00 mmol) in tetrahydrofuran (4 mL) for 20 min. After 30 min., a solution of 2-(2-chlorophenyl)-4-iodomethyl-5-isopropyloxazole (362 mg, 1.00 mmol) in tetrahydrofuran (4 mL) was added, and the resulting mixture was heated for 24 hours under reflux. The reaction mixture was allowed to reach room temperature, poured into water, and extracted with ethyl acetate. The organic layer was successively washed with water and saturated brine, dried over sodium sulfate, filtered, and concentrated. To the residue were added acetic acid (3 mL) and conc. hydrochloric acid (0.8 mL), and the resulting mixture was heated for 24 hours under reflux. The reaction mixture was allowed to reach room temperature, poured into a saturated aqueous sodium hydrogen carbonate solution, and extracted with ethyl acetate. The organic layer was successively washed with water and saturated brine, dried over sodium sulfate, filtered, and concentrated. The residue was purified by flash column chromatography on silica gel (hexane/ethyl acetate=5/1), to obtain the desired compound (256 mg, 64%).

$^1$H NMR (CDCl$_3$, 400 MHz) δ: 1.31 (d, 6H, J=7 Hz), 2.99 (t, 2H, J=7 Hz), 3.18 (m, 1H), 3.40 (t, 2H, J=7 Hz), 4.60 (s, 2H), 7.3–7.4 (m, 2H), 7.4–7.5 (m, 3H), 7.9–8.0 (m, 1H), 7.98 (d, 2H, J=8 Hz)

(2) [4-[3-[2-(2-Chlorophenyl)-5-isopropyloxazol-4-yl]propionyl]phenyl]acetonitrile In acetone (2 mL) was dissolved 1-[(4-chloromethyl)-phenyl]-3-[2-(2-chlorophenyl)-5-isopropyloxazol-4-yl]-propan-1-one (253 mg, 0.629 mmol). To the solution were added sodium iodide (94 mg, 0.629 mmol) and sodium cyanide (51 mg, 0.943 mmol). The resulting mixture was heated overnight under reflux. The reaction mixture was allowed to reach room temperature, poured into water, and extracted with ethyl acetate. The organic layer was successively washed with water and saturated brine, dried over sodium sulfate, filtered, and concentrated. The residue was purified by flash column chromatography on silica gel (hexane/ethyl acetate=3/1), to obtain the desired compound (44 mg, 18%).

$^1$H NMR (CDCl$_3$, 400 MHz) δ: 1.31 (d, 6H, J=7 Hz); 2.99 (t, 2H, J=7 Hz), 3.18 (m, 1H), 3.41 (t, 2H, J=7 Hz), 3.80 (s, 2H), 7.3–7.4 (m, 2H), 7.42 (d, 2H, J=8 Hz), 7.4–7.5 (m, 1H), 7.9–8.0 (m, 1H), 8.01 (d, 2H, J=8 Hz)

(3) [4-[3-[2-(2-Chlorophenyl)-5-isopropyloxazol-4-yl]-propionyl]phenyl]acetic acid In a mixture of conc. sulfuric acid and water (2/1, v/v, 1.5 mL) was suspended [4-[3-[2-(2-chlorophenyl)-5-isopropyloxazol-4-yl]propionyl]phenyl]acetonitrile (43 mg, 0.109 mmol). The suspension was stirred at 100° C. for 10 hours. The reaction mixture was allowed to reach room temperature, poured into an ice-water mixture, and extracted with chloroform. The organic layer was washed successively with water and saturated brine, dried over sodium sulfate, filtered, and concentrated. The residue was purified by flash column chromatography on silica gel (chloroform/methanol=100/0→97/3), to obtain the desired compound (28 mg, 61%).

$^1$H NMR (CDCl$_3$, 400 MHz) δ: 1.30 (d, 6H, J=7 Hz), 2.97 (t, 2H, J=7 Hz), 3.19 (m, 1H), 3.35 (t, 2H, J=7 Hz), 3.67 (s, 2H), 7.3–7.4 (m, 4H), 7.4–7.5 (m, 1H), 7.8–8.0 (m, 3H)

EXAMPLE 3

(Pharmacological Tests)

I. Method of Measurement (1) Measurement of PPARγ, δ Transactivation Activity

Each of PPARγ & δ transactivation activities of the tested compound [compound of Example 1 and known PPARγ agonist (Rosiglitazone) and known PPARδ agonist (L-165041)] was measured in the manner described below.

1) Material

CV-1 was obtained from Tohoku University Aging Medical Laboratory, Medical Cell Collection Center. All test compounds were dissolved in dimethylsulfoxide (DMSO) to give a test sample of 0.1% concentration.

2) Plasmid

Receptor expression plasmid (GAL4-hPPARγ LBD, GAL4-hPPARδ LBD), Luciferase expression plasmid (UASx4-TK-LUC), and β-galactosidase expression plasmid (βGAL) similar to Kliewer, S. A., et al., ((1992) Nature, 358:771–774) were employed.

3) Transfection

CV-1 cells were seeded in 24 well culture plates at 2×10$^5$ cells per well, and cultured for 24 hours using 4%-fetal bovine serum (FBS)-added OPTI-MEM I Reduced Serum Medium (Life Technologies, 500 μL/well). Subsequently, the cells were washed with non serum-added OPTI-MEM. To the washed cells were added DNA-containing solution [the following components were contained in the one well solution (250 μl): 0.03 μg of GAL4-hPPARδ LBD, 0.25 μg of UASx4-TK-LUC, 0.35 μg of βGAL, and 2 μL of lipofection reagent, DMRIE-C (Life Technologies). These components were dissolved in OPTI-MEM and allowed to stand for 30 minutes at room temperature]. The cells were incubated for 5 hours at 37° C.

4) Cell Treatment by Addition of Test Compound

The cells were then incubated for 40 hours in 500 μL of fresh OPTI-MEM containing 4% FBS and the test compound (dissolved in 100% DMSO to reach a final concentration: 10$^{-4}$M or 10$^{-5}$M)

5) Measurement of Reporter Gene Expression Level

The culture medium was removed and the cells were washed with PBS twice. Cell lysates were produced using a solubilizing buffer (25 mM Tris-PO$_4$ (pH 7.8), 15% v/v glycerol, 2% CHAPS, 1% Lecithin, 1% BSA, 4 mM EGTA (pH 8.0), 8 mM MgCl$_2$, 1 mM DTT). A portion (20 μL) of the solution was transferred onto a 96-well plate. Subsequently, 100 μL of luciferase substrate solution (Piccagene: available from Nippon Gene Co., Ltd.) was added, and a luminous intensity per one sec. (luciferase activity) was measured by means of MLR-100 type Microluminoreader (available from Corona Electrics Co., Ltd.). Further, the activity caused by βGAL incorporation which was incorporated into the cells simultaneously with the incorporation of the luciferase gene was measured, for correcting variation of luciferase activity by the addition of the compound, utilizing the transfection efficiency of the incorporated gene. β-Galactosidase activity was measured by the following method:

50 μL of the solubilized sample was placed on another 96-well plate; 10 μL of ONPG (2-nitrophenyl-β-galactopyranoside) solution was added; incubation was carried out for 5 minutes at room temperature; 50 μL of a reaction stopping solution (1M sodium carbonate solution) was added; and the absorbance at 414 nm was measured. A relative PPAR activity was calculated based on the following: 0% (luciferase activity (control value) of cells treated with DMSO (0.1% concentration, solvent) alone), 100% (luciferase activity of cells treated with a control reagent (PPARγ: 10$^{-5}$ M Rosiglitazone, PPARδ: 10$^{-4}$ M L-165041)).

II. Results

The compound of the invention described in Example 1 showed PPAR activity (expressed by a relative value of the tested compound at 10$^{-5}$ M, obtained by setting the result of the control to 100%) of 50 for PPARγ and 93±3 for PPARδ.

As is apparent from the above-mentioned test results, it has been confirmed that the compound of the invention has excellent PPAR activating effect.

What is claimed is:

1. A phenylacetic-acid derivative having the following formula (I) or a salt thereof:

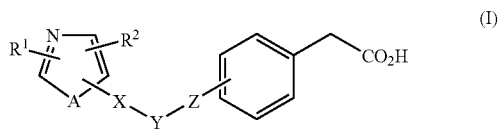

wherein each of $R^1$ and $R^2$ independently is a hydrogen atom, a halogen atom, nitro, an alkyl group having 1–8 carbon atoms, an alkoxy group having 1–8 carbon atoms, an alkyl group having 1–8 carbon atoms which has 1 to 3 halogen substituents, an alkoxy group having 1–8 carbon atoms which has 1 to 3 halogen substituents, an alkenyl group having 2–8 carbon atoms, an alkynyl group having 2–8 carbon atoms, a 3–7 membered cycloalkyl group, an alkyl group having 1–8 carbon atom which has a 3–7 membered cycloalkyl substituent, an aryl group having 6–10 carbon atoms which optionally has a substituent, an arylalkyl group which has a $C_{6-10}$ aryl portion and $C_{1-8}$ alkyl portion, a heterocyclic group which optionally has a substituent, or a heterocyclic-alkyl group having an alkyl group of 1–8 carbon atoms;

A is an oxygen atom, a sulfur atom;

each of X and Z independently is —C(=O)—, —C(=O)NH—, —C(=N—OR$^4$)—, —CH(OR$^5$)—, —NH(C=O)—, —NHSO$_2$—, —SO$_2$NH—, —CH=CH—, —C=C—, or a bond in which each of R$^4$ and R$^5$ is a hydrogen atom or an alkyl group having 1–8 carbon atoms; and Y is an alkylene chain having 1–8 carbon atoms.

2. A phenylacetic acid derivative having the following formula (II) or a salt thereof:

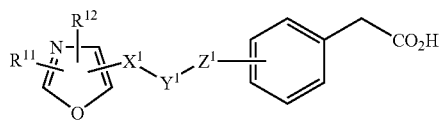

(II)

wherein
each of $R^{11}$ and $R^{12}$ independently is a hydrogen atom, a halogen atom, nitro, hydroxyl, amino, an alkyl group having 1–8 carbon atoms, an alkoxy group having 1–8 carbon atoms, an alkyl group having 1–8 carbon atoms which has 1 to 3 halogen substituents, an alkoxy group having 1–8 carbon atoms which has 1 to 3 halogen substituents, an alkenyl group having 2–8 carbon atoms, an alkynyl group having 2–8 carbon atoms, a 3–7 membered cycloalkyl group, an alkyl group having 1–8 carbon atoms which has a 3–7 membered cycloalkyl substituent, or a phenyl, naphthyl, benzyl, phenethyl, pyridyl, thienyl, furyl, quinolyl, or benzothienyl group which optionally has a substituent selected from the group consisting of a halogen atom, nitro, hydroxyl, amino, an alkyl group having 1–8 carbon atoms, an alkoxy group having 1–8 carbon atoms, an alkyl group having 1–8 carbon atoms which has 1 to 3 halogen substituents, an alkoxy group having 1–8 carbon atoms which has 1 to 3 halogen substituents, an alkenyl group having 2–8 carbon atoms, an alkynyl group having 2–8 carbon atoms, a 3–7 membered cycloalkyl group, an alkyl group having 1–8 carbon atoms which has a 3–7 membered cycloalkyl substituent, phenyl and pyridyl;

each of $X^1$ and $Z^1$ independently is —C(=O)—, —C(=O)NH—, —C(=N—OR$^{14}$)—, —CH(OR$^{15}$)—, —NH(C=O)—, —NHSO$_2$—, —SO$_2$NH—, —CH=CH—, —C≡C—, or a bond in which each of $R^{14}$ and $R^{15}$ is a hydrogen atom or an alkyl group having 1–8 carbon atoms; and $Y^1$ is an alkylene chain having 1–8 carbon atoms.

3. The phenylacetic acid derivative or a salt thereof defined in claim 2, wherein $X^1$ is a bond, and $Z^1$ is —C(=O)—.

4. A pharmaceutical composition comprising a phenylacetic-acid or salt thereof as defined in any one of claims 1 to 3 and a pharmaceutically acceptable carrier.

\* \* \* \* \*